Figure 1:
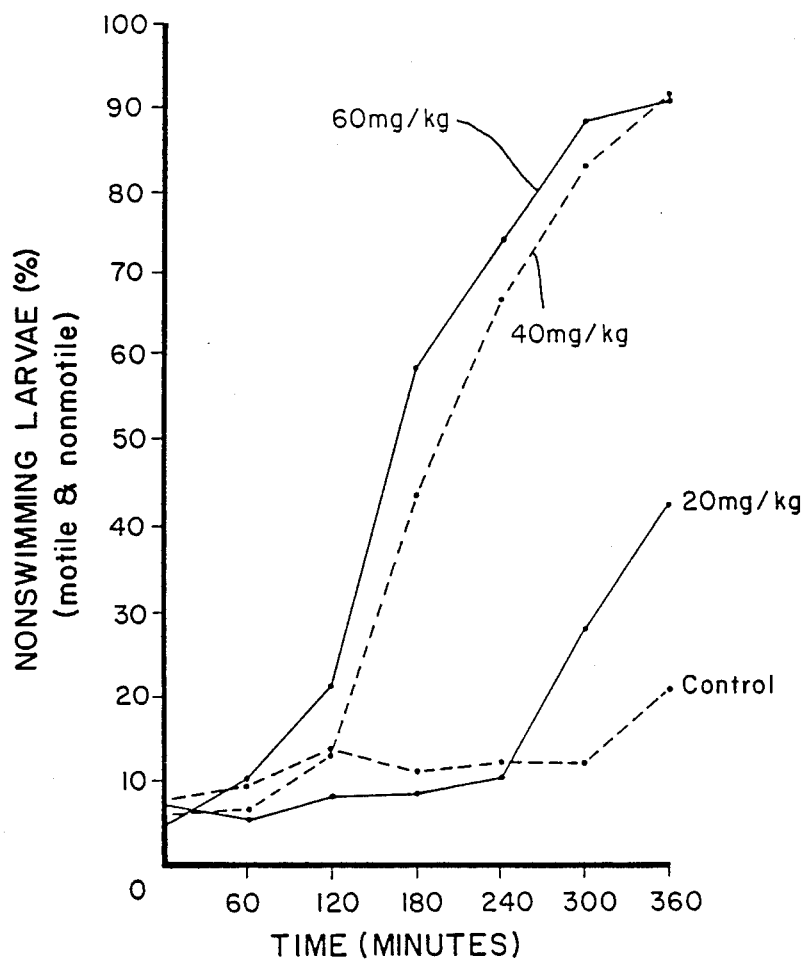

United States Patent [19]

Heitz et al.

[11] Patent Number: 4,846,788

[45] Date of Patent: Jul. 11, 1989

[54] COMBATTING INTERNAL PARASITES IN WARM BLOODED ANIMALS

[75] Inventors: James R. Heitz; James A. Hawkins, both of Starkville, Miss.

[73] Assignee: L. S. van Landingham, Jr., Potomac, Md.

[21] Appl. No.: 195,875

[22] Filed: May 19, 1988

Related U.S. Application Data

[63] Continuation of Ser. No. 399,813, Jul. 19, 1982.

[51] Int. Cl.[4] ............................................. A61N 1/30
[52] U.S. Cl. ...................................... 604/20; 604/49; 514/454
[58] Field of Search ..................... 604/20, 49; 514/454

[56] References Cited

U.S. PATENT DOCUMENTS 3,629,390  12/1971  Wentworth ..................... 514/454 X
4,320,140   3/1982  Crounse et al. ................... 514/454

Primary Examiner—John D. Yasko
Attorney, Agent, or Firm—L. S. van Landingham, Jr.

[57] ABSTRACT

Dyes which, in the presence of molecular oxygen, promote the formation of cytotoxic oxygen are used to combat internal parasites in warm blooded animals. Internal parasites having the dye incorporated therein are exposed to electromagnetic radiation to initiate one or more lethal oxidative reactions. The photosensitized parasites may be in the infective stage thereby breaking the life cycle. This reduces or prevents reinfection and the need for traditional anthelmintics.

20 Claims, 6 Drawing Sheets ic application is a continuation application of pending application Ser. No. 399,813, Filed July 19, 1982 on behalf of James R. Heitz and James A. Hawkins for Combatting Internal Parasites In warm Blooded Animals.

COMBATTING INTERNAL PARASITES IN WARM BLOODED ANIMALS

This application is a continuation application of pending application Ser. No. 399,813, Filed July 19, 1982 on behalf of James R. Heitz and James A. Hawkins for Combatting Internal Parasites In warm Blooded Animals.

THE BACKGROUND OF THE INVENTION

1. The Field of The Invention

This invention broadly relates to a novel method of combatting internal parasites in warm blooded animals. In some of its more specific aspects, the invention is concerned with a method which utilizes certain dyes and exposure to electromagnetic radiation to initiate one or more lethal oxidative reactions in the internal parasites thereby breaking the life cycle.

2. The Prior Art

Xanthene dyes have been used heretofore as insecticides. For instance, U.S. Pat. No. 4,320,140 discloses a composition containing an insecticidally effective amount of Rose Bengal and/or erythrosin and a synergistically effective amount of fluorescein. The resulting synergistic insecticidal composition is said to be effective against insects of the families Muscidae and Culicidae.

The "Description of the Prior Art" appearing in Columns 1 and 2 of U.S. Pat. No. 4,320,140, which is incorporated herein by reference, described six prior art publications relating primarily to the use of Xanthene dyes as insecticides. These publications and U.S. Pat. No. 4,320,140 are not concerned with endoparasitic helminths or pathogenic gastrointestinal protozoa.

THE SUMMARY OF THE INVENTION

The present invention utilizes the dyes described hereinafter and exposure to electromagnetic radiation to initiate one or more lethal photo-oxidative reactions in certain internal parasites of warm blooded animals. The parasites are endoparasitic helminths and/or pathogenic gastrointestinal protozoa having a life cycle which includes a life stage within the animals and a life stage outside of the animals. The parasites are normally protected from exposure to natural electromagnetic radiation having a wave length falling within the visible spectrum during at least most of the life stage within the animals, but they are normally exposed to electromagnetic radiation during at least a portion of the life stage outside of the animals.

In practicing the method of the invention, the internal parasites are caused to incorporate therein a photosensitizing amount of a dye which, in the present of molecular oxygen, promotes the formation of cytotoxic oxygen upon exposure to electromagnetic radiation of a wave length absorbed thereby. Thereafter the parasites having the dye incorporated therein are exposed to electromagnetic radiation of a wave length absorbed by the dye to thereby form cytotoxic oxygen and initiate at least one lethal oxidative reaction within the resulting photosensitized parasites. The parasites are preferably in the infective stage, thereby causing the life cycle to be broken. This markedly reduces or prevents reinfection and the need for treating the animals with traditional anthelmintics.

THE BRIEF DESCRIPTION OF THE ACCOMPANYING DRAWINGS

Several important features and aspects of the invention are further illustrated by the accompanying drawings, wherein FIGS. 1–6 are graphs prepared from the data appearing in Tables I–VI, respectively, as is discussed in greater detail hereinafter in Examples 1–4.

THE DETAILED DESCRIPTION OF THE INVENTION INCLUDING THE PRESENTLY PREFERRED VARIANTS AND EMBODIMENTS THEREOF

It will be appreciated by those skilled in this art that there are certain presently preferred variants and embodiments of the present invention. Accordingly, the invention will be discussed hereinafter in greater detail with respect to, for example, the parasites to be combatted, the animal hosts therefor, the dyes to be used, and the presently preferred techniques and conditions to be employed in practicing the method.

THE INTERNAL PARASITES

The internal parasites which may be combatted or controlled in practicing the present invention include the endoparasitic helminths and the endopathogenic protozoa. The invention is especially useful in combatting and controlling endoparasitic helminths which reside in or pass through the gastrointestinal tract as adults or as an immature or larvae stage or stages, or which pass through the gastrointestinal tract in the form of eggs that may later hatch and develop into an immature stage or larvae. Some important examples are the endoparasitic Nematoda or roundworms, including the Metastrongylidea, Ascaroidea, Trichostrongyloidea, Strongyloidea, Trichuroidea, Oxyuroidea, and Rhabditoidea; and the endoparasitic platyhelminths or flatworms, including the Cestoda and Trematoda. A number of the aforementioned internal parasites are often commonly referred to as roundworms, pinworms, tapeworms, hookworms, lung worms, and flukes such as liver, stomach and pancreatic flukes.

The internal or gastrointestinal pathogenic protozoa include the Amoebidae and the Coccidia. The Coccidia and especially Eimeria and Isospora spp. cause coccidiosis in cattle, horses, sheep, goats, swine, dogs, cats, poultry and birds. Diseases of this type include those referred to as ruminant coccidiosis, which occurs in ruminant animals, and gastrointestinal coccidiosis or cecal coccidiosis which occurs in poultry and birds. Some specific species include *Eimeria necatrix* and *Eimeria tenella* which cause coccidiosis in poultry and birds. The pathogenic Amoebidae include *Entamoeba histolytica*.

The aforementioned internal parasites to be combatted in practicing the method of the invention should have a life cycle which include a life stage within the host animal and a life stage outside of the host animal. the parasites are protected from exposure to natural electromagnetic radiation having a wave length falling within the visible spectrum during at least most, and preferably all or substantially all, of the life stage within the host animal. However, the parasites are normally exposed to electromagnetic radiation, which is usually natural or artificial visible light, during at least a portion of their life stage outside of the host animal. The parasites to be combatted are also capable of absorbing, ingesting, assimilating or otherwise incorporating therein a photosensitizing amount of a dye described herein which in the presence of molecular oxygen, promotes the formation of cytotoxic oxygen upon exposure to electromagnetic radiation absorbed thereby, which is usually visible light.

The well-known authoritative text entitled *The Merck Veterinary Manual*, Fifth Edition (1979), contains a detailed discussion of the parasitic diseases of the common domestic animals caused by the endoparasitic helminths and endopathogenic protozoa. Numerous examples are given of species causing these parasitic diseases. This text, and especially Pages 671–728 and 1122–1139, is incorporated herein by reference.

THE WARM BLOODED ANIMALS

The term warm blooded animal(s) is used herein in its usual scientific sense. The term embraces vertebrates such as the Mammalia and the Aves whose blood remains at a relatively constant temperature, such as for example from about 98° F. to 112° F., irrespective of the temperature of the surrounding medium. The warm blooded animals may be either domesticated or in the wild, semi-wild or untamed state, but the treatment of domestic animals is of the greatest importance from the commercial standpoint. Some examples of warm blooded animals include the Ruminantia, such as cattle, bison, buffalo, sheep, goats, chamois, deer, antelopes, giraffes, camels, chevrotains, etc.; the Equidae such as hores, asses, donkeys, mules, zebras, etc.; the Suidae, such as domestic swine or hogs, wild or semi-wild bores or razorbacks, etc.; the Galliformes, including domestic poultry such as chickens, turkeys, domestic ducks, domestic geese and guinea fowl, and wild or semi-wild gallinaceous birds such as pheasants, grouse, quail, wild ducks, wild geese, partridges, snipe, etc.; the Canidae, including for example dogs, foxes, coyotes, wolves, jackals and hyenas; and the Felidae, including for example cats, lions, tigers, leopards, lynxes and jaguars.

THE DYES

The term "dye(s)" is intended to embrace those compounds, as more particularly defined hereinafter, which are capable of absorbing electromagnetic radiation having a wave length falling within the visible spectrum, i.e., from about 4000 to 8000 Angstrom units. The compounds may also absorb electromagnetic radiation having wave lengths falling outside of the visible spectrum, and especially in the near infrared and in the near and medium to far ultraviolet ends of the visible ends of the spectrum. The compounds are usually colored due to the presence of one or more chromophore groups which absorb electromagnetic radiation having a wave length falling within the visible spectrum, and they are often useful as colorants in the commercial sense. However, it is understood that the term dye(s) is also intended to include all compounds which are useful in practicing the present invention, and whether or not they are commercially useful as colorants.

Numerous members of the various classes of prior art dyes suitable for use in practicing the present invention are disclosed in the authoritative publication *Colour Index*, Third Edition, published by the Society of Dyers and Colourists, London, England. All known classes of dyes are arranged in the various volumes of this publication by number, with each of the individual dyes being assigned a specific number known as a "Colour Index Number" or "C.I. No.". The publication includes the structural formula for each of the dyes, and also additional information including references to other publications and patent numbers referring to that particular dye. Thus, by giving a Colour Index Number, one may positively identify a specific dye by name and structural formula, and also provide additional references concerned with that particular dye. In view of the large amount of information contained therein, the *Colour Index* is incorporated herein by reference. The various publications, United States patents and foreign patents set out in the *Colour Index* for each of the dyes are likewise incorporated herein by reference. A number of the dyes discussed hereinafter will be referred to by their Colour Index Number. Also, certain dyes or classes of dyes will be disclosed hereinafter by their Colour Index Number with the view of shortening the applicants' specification.

The xanthene derivatives, and especially the xanthene dyes having colour index numbers of 45000–45999, are present preferred in practicing the invention. The xanthene dyes are disclosed on Pages 4417–4430 of the aforementioned publication entitled Colour Index, and reference may be had thereto for numerous specific xanthene dyes. Additional xanthene dyes include those prior art derivatives of xanthene per se which absorb electromagnetic radiation having wave lengths falling within the ranges set out above. The derivatives of fluorescein (C.I. No. 45350) having one or more substituents in the 4, 5, 6, 7, 2′, 4′, 5′ and 7′ positions selected from the group consisting of F, Cl, Br, I, $-NO_2$, $-COOH$ and $-OH$ are especially important Specific examples of presently preferred xanthene dyes include erythrosin B (C.I. No. 45430), phloxin B (C.I. No. 45410), eosin yellowish (C.I. No. 45380), Rose Bengal (C.I. No. 45440) and rhodamine B (C.I. No. 45170).

A large class of dyes are know which have been found to promote or catalyze the formation of cytotoxic oxygen in the presence of molecular oxygen and electromagnetic radiation. These dyes are of the art-recognized class known as sensitizing dyes for photograhic film, and to a lesser extend, desensitizing dyes for photographic film. United States patents relating to the sensitizing dyes are classified in Class 430, subclasses 570–595, and United States patents relating to the desensitizing dyes are classified in Class 430, subclass 606. The United States patents classified therein are incorporated herein by reference.

Still other sensitizing and desensitizing dyes for photographic film are disclosed in the well-known text entitled *The Cyanine Dyes and Related Compounds* by F. M. Hammer. This text and the references cited therein are likewise incorporated herein by reference.

The authoritative texts entitled *Photography, Its Materials and Processes,* by C. B. Neblette, Fifth Edition, and especially Pages 125–147 and 185 thereof; and *The Theory Of The Photographic Process,* Fourth Edition, and especially Pages 161–169 and 252–268 thereof, disclose still other sensitizing and desensitizing dyes for photographic film. These two texts and the references cited therein are also incorporated herein by reference.

Some of the more important classes of the sensitizing dyes include the cyanine dyes, the merocyanine dyes, the azo dyes, the triphenyl methane dyes, the polycarbocyanine dyes, the hemioxanol dyes, the hemicyanine dyes, the acridine dyes, and the anthraquinone dyes. Numerous specific examples of these dyes are found in the *Colour Index* and the aforementioned United States patents and texts, which are incorporated herein by reference. However, some typical examples include ethyl violet, Fast Red, Congo Red, Glycine Red, Benzo Nitrol Brown, Quinoline Blue, Acridine Orange and Alizorin Blue.

Mixtures of two or more of the dyes disclosed herein may be used, and especially of dyes having different absorption spectra. Mixtures of certain sensitizing and synergistic nonsensitizing dyes may be used to achieve the "supersensitization" disclosed in U.S. Pat. Nos. 2,075,046, 2,075,047 and 2,075,048. Examples of the latter mixtures include auramine and carbocyanines. It is usually preferred that the dyes used herein be water soluble.

The dyes may be orally administered to the animals in an amount effective to cause the photosensitization of the parasites in the presence of electromagnetic radiation absorbed thereby. Usually about 0.01-100 mg/kg, or for better results about 10-60 mg/kg, and preferably about 20-40 mg/kg based on body weight is administered. These quantities may be administered on a daily basis and over a period of time sufficient to achieve the desired level of incorporated dye in the parasites. If desired, sustained. release formulations may be employed which release therapeutically effective amounts of the dye over a prolonged period of time, such as 5-60 days or longer. Formulations of this type are disclosed in U.S. Pat. Nos. 4,044,119 and 4,196,187, which are incorporated herein by reference.

The dye may be administered to the animal in the form of an additive to its daily feed ration, in capsules, compressed pellets, boluses, salt blocks and the like. In the case of poultry, the dye may be incorporated within a synthetic grit, such as disclosed in U.S. Pat. No. 3,629,390, to thereby achieve sustained release of the dye over an extended period of time. U.S. Pat. No. 3,629,390 is incorporated herein by reference. Pallets or particles of the dye provided with a light impervious coating often produce improved results as photodegradation of the dye is prevented.

One or more of the dyes described herein may be used in combination with prior art conventional anthelmintics, such as piperazine, diethylcarbamazine, or a protected benzimidazole. In such instances, the dye may be orally administered in the quantites mentioned herein and the conventional anthelmintics may be orally administered in the recommended prior art dosages. However, it is understood that smaller or larger effective doses may be employed when desired. The dyes described herein may be employed in any effective form, such as in the free acid or salt forms, or in the form of simple derivatives.

As a general rule, the endoparasitic helminths usually reside in the gastrointestinal tract as adults and produce large numbers of eggs which are passed from the animal host in the feces. The eggs normally hatch in the feces, and then develop into one or more immature larvae stages while within the feces. The infective stage, which is often referred to as third stage larvae, escape or wander from the fecal pat and climb onto nearby foliage blades or other food sources for the host animal, and they are ingested by the feeding animal host. The ingested infective larvae pass into the gastrointestinal tract where they develop in to the adult stage. The resulting new generation of adult nematodes then proceeds to lay additional eggs whereby the life cycle is continued. When the host animal is fed the dye described herein, the dye is admixed with the food to be digested and passes through the gastrointestinal tract. The dye is in contact with the exposed skin of the immature larvae stages and adult stages residing in the gastrointestinal tract, and it is also present in the food consumed by the adult nematodes. As a result, the nematodes in the immature larvae stages and/or adult stage appear to ingest, assimilate, absorb or otherwise incorporate the dye into their tissues. Surprisingly, the dye is also present within the eggs that are produced by the adult nematodes. The feces contain substantially all of the administered dye that is not incorporated in the larvae and adult nematodes residing in the gastrointestinal tract or in the eggs. The fecal pats are normally exposed to visible light, and the hatching eggs and larvae stages developing therefrom are likewise exposed to visible light at some stage of their development. The large amounts of dye present initially in the eggs and incorporated in the developing larvae feeding in the dye containing fecal pat result in one or more lethal oxidative reactions when exposed ot visible light. As a result, the hatchability rate of the eggs is lowered markedly, and the survival rate of any developing larvae is very low. In the presence of visible light, substantially all of the larvae are killed before they are able to reinfect the animal host.

As is well known, coccidiosis disease is transmitted by infective sporulated oocysts which develop initially in the gastrointestinal tract as unsporulated oocysts. The male and female cells before fertilization, the subsequently produced fertilized cells or zygotes, and the unsporulated oocysts absorb or otherwise incorporate large amounts of the dye while within the gastrointestinal tract. The unsporulated oocysts are not infective as produced in the gastrointestinal tract or as passed in the feces. The oocysts must become sporulated under favorable environmental conditions outside of the animal, and usually in the presence of visible light, before they are infective. The large amounts of dye absorbed or incorporated therein, when in the presence of visible light, initiates or causes one or more lethal oxidative reactions which tend to prevent the unsporulated oocysts from becoming sporulated, i.e., infective. In instances where sporulation does occur, then the sporozoites contained therein tend to be demobilized or killed and are thereby prevented from infecting the animal.

The pathogenic *Entamoeba histolytica* absorb or incorporate the dye while in the gastrointestinal tract. After passing in the feces, the infective stage is usually exposed to visible light. The dye initiates or causes one or more lethal oxidative reactions at that time which tend to kill the infective stage and prevent infection.

The toxicological mechanism involved in practicing the method of the inventions not fully understood in all respects at the present time. However, it appears that the primary toxicological mechanism involves the absorption of electromagnetic energy by the dye moleculse which are incorporated in the parasites, followed by transfer of the absorbed energy from the dye molecules to the nearby oxygen molecules which are normally present in the parasite tissues. Photoelectrons may also be transferred to the oxygen molecules and accepted thereby to form negatively charged free radicals. The resultant oxygen molecules are in an excited highly reactive state, and are capable of entering into one or more lethal oxidative reactions with different types of subcellular biomolecules present in the adjacent parasite tissues. Thus, the dye molecules incorporated within the parasites promote or catalyze the formation of cytotoxic oxygen upon exposure to electromagnetic radiation of a wave length absorbed thereby. The specific subcellular biomolecules which react with the cytotoxic oxygen are unknown at the present time. In fact, it presently appears that the lethal oxidative reaction may be the cumulative effect of many nonspecific oxidation reactions which ultimately result in the death of the parasite.

It also appears at the present time that several well known species of cytotoxic oxygen may be formed upon exposure of the dye to the electromagnetic radiation. Some examples of cytotoxic oxygen species include (1) singlet oxygen, wherein an oxygen molecule has been raised to the first excited singlet state by transfer of absorbed electromagnetic energy from a photoexcited dye molecule to an oxygen molecule; (2) the free superoxide radical $O_2^-$, *which is formed when oxygen molecules accept photoelectrons that are transiently trapped by the dye molecules and then transferred to the oxygen molecules*; (3) the free peroxy anion, which may be written as $O_2^{--}$; *and* (4) the free hydroxyl radical, which may be written as $OH\cdot$. All of these species of cytotoxic oxygen are excellent oxidizing agents and are capable of entering into oxidizing reactions with may types of subcellular biomolecules present in the photosensitized parasite. The resulting lethal oxidative reaction occurs very rapidly and death usually follows within a few minutes to a few hours.

There is also a secondary toxicological mechanism which appears to be independent of electromagnetic radiation. This reaction, which occurs in the dark, is a much slower process. However, it does adversely affect the parasite and may ultimately result in its death even in the absence of electromagnetic radiation.

The above described primary and secondary toxicological mechanisms are especially effective against the infective stage of the parasite thereby allowing the life cycle of the parasites to be broken in a very rapid and effective manner. The primary and secondary toxicological mechanisms are also effective against the various non-infective parasite stages and the adult parasites. Practicing the method of the invention adversely affects the adult parasite's viability and fecundity, egg-hatchability, and larval survival prior to and after reaching the infective stage. As a result, the present invention is capable of markedly reducing or even preventing reinfection of the animal hosts, and the invention also greatly reduces or in some cases eliminates the need for traditional anthelmintics.

The foregoing detailed description, the accompanying figures of the drawings, and the following specific examples are for purposes of illustration only, and are not intended as being limited to the spirit or scope of the appended claims.

EXAMPLE 1

Eight heavily parasitized mixed breed calves with naturally acquired mixed bovine gastrointestinal nematode infections were treated per os with erythrosin B at 20, 40 and 60 mg/kg body weight. It was determined by necropsy and actual worm counts that the various species of adult nematodes infecting the calves were present in the following average percentages: *Ostertagia ostertagi* 31.5%; *Trichostrongylus sp.* 18.6%; *Cooperia sp.* 46.3%; *Oesophagostomum radiatum* 3.1% *Bunosomum phlebotomum* 0.2%; Haemonchus sp. 0.1%; and *Trichuris sp.* 0.2%. Two calves were treated at each dosage level, and two calves served as untreated controls. Fecal samples were collected daily from each of the eight calves.

Fecal material from each of the above samples was incubated for 15 days in the dark, at which time nematodes were present as third stage larvae. The larvae were removed from each of the incubated samples of the fecal material by Baermannization, and the larvae from each sample was placed in a separate standard petri dish at levels of approximately 75 larvae per dish. Each dish, which corresponded to treatment at one of the four different dye level concentrations, was exposed to fluorescent light from a pair of 40W Westinghouse Cool White bulbs. The light intensity was measured by photometer and was found to be approximately 1250$\mu$ Einsteins/cm$^2$ sec at the surface of the petri dish. Prior to light exposure and at hourly intervals thereafter, the effect of the dye on the larvae was scored twice for each dish, the average value was calculated and recorded, and the dish was discharged thereafter.

Each larvae was scored as either actively swimming (normal) or non-swimming. The non-swimming category was further classified as either motile but not swimming, or as completely non-motile (dead). Therefore, the larvae were initially classified into one of the following three categories: (1) swimming (normal); (2) motile non-swimming; or (3) non-motile (dead).

Numerous observations confirmed the fact that motile non-swimming larvae eventually became non-motile and that non-motile larvae were dead or dying. In view of this, the data are presented as percent non-swimming larvae, which includes both categories 2 and 3. Obviously a non-motile larvae (category 3) will not be physically above to move up from a fecal pat in which it was incubated and onto the blades of grass in a pasture and infect a grazing animal. Similarly, motile non-swimming larvae (category 2) which are only slightly motile most likely will not be able to maintain enough normal physical activity to reach the grass blades and be ingested and infect grazing animals.

The above experimental procedure was repeated a total of six times and the data were averaged. The data thus obtained are presented hereinafter in Table I. The data of Table I show that, after as little as 3 hours of light exposure, markedly more dye treated larvae are non-swimming than control larvae. After 5-6 hours of light exposure, 90 percent or more of the higher dosed larvae are non-swimming.

TABLE I

The effect of erythrosin B on 3rd stage larvae of gastrointestinal nematodes of cattle showing percent non-swimming larvae at several dosage rates as a function of time of light exposure. These larvae had been in culture for 15 days prior to exposure to light.

| EXPOSURE IN MINUTES | TREATMENT DOSE | | | |
|---|---|---|---|---|
| | 1 Control | 2 20 mg/kg | 3 40 mg/kg | 4 60 mg/kg |
| 0 | 7.60 | 6.72 | 5.54 | 4.40 |
| 60 | 10.03 | 5.78 | 6.68 | 10.63 |
| 120 | 13.82 | 7.36 | 13.26 | 21.85 |
| 180 | 11.61 | 7.73 | 44.30 | 59.32 |
| 240 | 12.68 | 10.40 | 68.86 | 75.38 |
| 300 | 13.17 | 28.73 | 83.65 | 89.79 |
| 360 | 21.67 | 41.73 | 92.23 | 91.63 |

The above experimental procedure was modified in a second series of runs to investigate the effects of increased exposure of the nematodes to the dye due to increased incubation time in the fecal material. In this second series of runs, larvae were cultured in the fecal material for 20 days prior to light exposure rather than 15 days, and all other parameters remained the same.

The data thus obtained are presented hereinafter in Table II. The data of Table II indicate that there is no noticeable difference between incubation for 15 days and 20 days.

TABLE II

The effect of erythrosin B on 3rd stage larvae of gastrointestinal nematodes of cattle showing percent non-swimming larvae as a function of time of light exposure. These larvae had been in culture for 20 days prior to exposure to light.

| EXPOSURE IN MINUTES | TREATMENT DOSE | | | |
|---|---|---|---|---|
| | 1 Control | 2 20 mg/kg | 3 40 mg/kg | 4 60 mg/kg |
| 0 | 8.76 | 7.88 | 6.90 | 2.25 |
| 60 | 10.39 | 10.86 | 10.11 | 6.47 |
| 120 | 10.55 | 13.23 | 17.20 | 25.05 |
| 180 | 18.49 | 10.19 | 34.87 | 55.18 |
| 240 | 15.44 | 24.84 | 59.25 | 71.82 |
| 300 | 18.22 | 35.32 | 87.71 | 87.71 |
| 360 | 20.58 | 32.51 | 90.79 | 92.09 |

The above experimental procedure was modified in a third series of runs to investigate the effects of still further increased exposure of the nematodes to the erythrosin B due to culture in the fecal material for 30 days rather than 15 to 20 days. All other parameters remained the same. The data thus obtained are presented hereinafter in Table III. The data of Table III show that incubation for 30 days results in a marked increase in the levels of non-swimming larvae for all dosage levels of erythrosin B.

TABLE III

The effect of erythrosin B on 3rd stage larvae of gastrointestinal nematodes of cattle showing percent non-swimming larvae as a function of time of light exposure. These larvae had been in culture for 30 days prior to exposure to light.

| EXPOSURE IN MINUTES | TREATMENT DOSE | | | |
|---|---|---|---|---|
| | 1 Control | 2 20 mg/kg | 3 40 mg/kg | 4 60 mg/kg |
| 0 | 10.4 | 6.7 | 7.6 | 8.5 |
| 60 | 13.3 | 8.4 | 14.6 | 14.6 |
| 120 | 17.5 | 12.7 | 26.8 | 44.7 |
| 180 | 16.7 | 23.9 | 49.1 | 76.3 |
| 240 | 12.6 | 49.4 | 73.8 | 91.7 |
| 300 | 21.9 | 63.5 | 86.1 | 95.9 |
| 360 | 23.7 | 74.7 | 95.1 | 97.1 |

Figure 2:
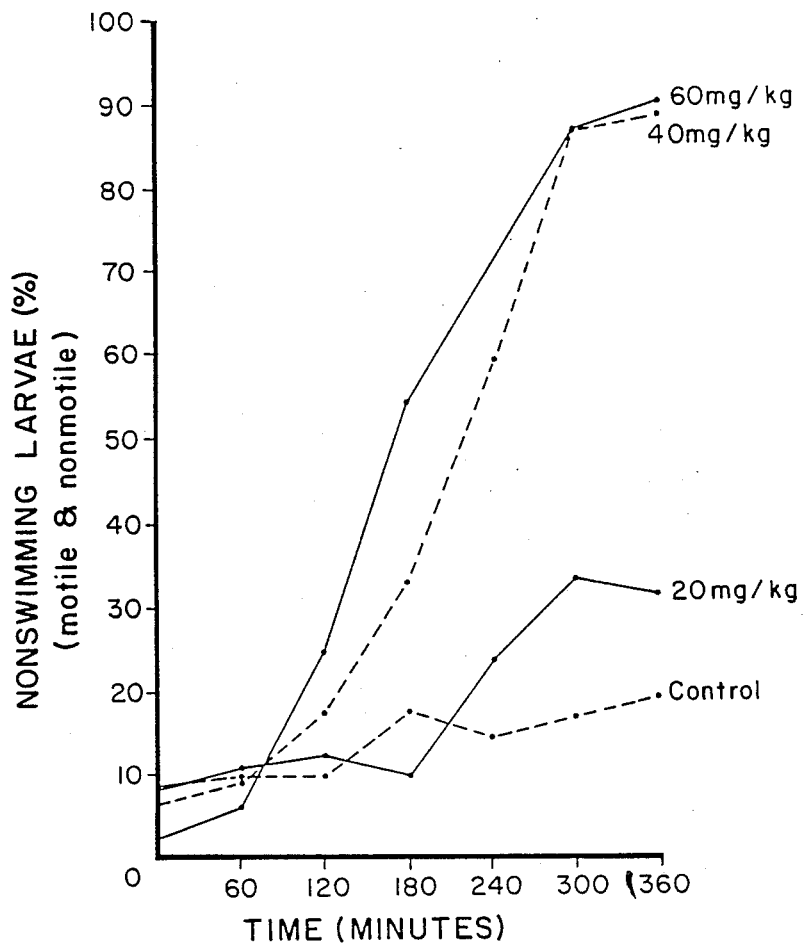
Figure 3:
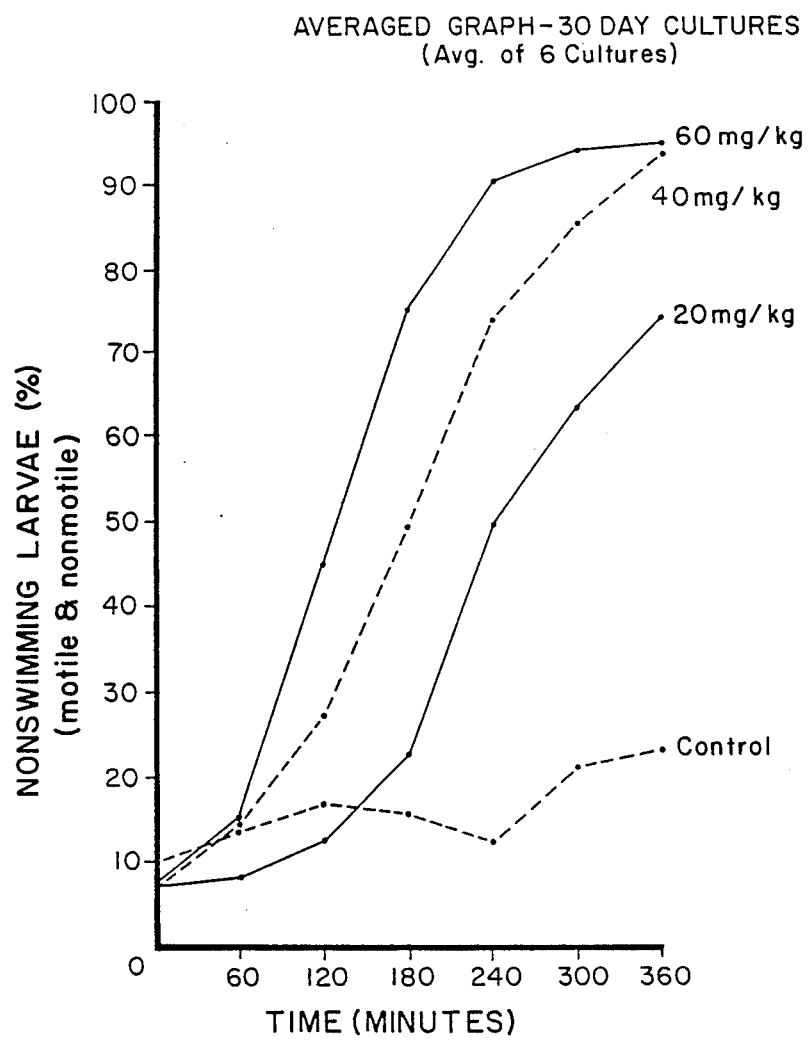

The data of Tables I, II and III were used in preparing the graphs of FIGS. 1, 2 and 3, respectively, of the drawings. Upon reference to FIGS. 1, 2 and 3, it may be seen the graphs appearing therein visually illustrate that erythrosin B at all dosage levels is capable of causing a toxic reaction in nematodes upon exposure to visible light. The toxic reaction is directly proportional to the dosage level of erythrosin B, the light exposure time, and the time of incubation prior to light exposure.

EXAMPLE 2

Feces were collected from a mixed breed calf of approximately 6 months of age naturally infected with bovine gastrointestinal nematodes. Vermiculite and tap water were added to the feces to form a mixture suitable for culture. Erythrosin B was then added directly to eight portions of the feces culture at concentrations of 125, 250, 500, 750, 1000, 1500, 2000, and 3000 mg/kg. An untreated ninth portion of the culture was maintained as a control. All nine cultures were maintained in the dark until the infective stage had developed (third stage larvae). Infective larvae were then collected from each culture by Baermannization and placed in separate standard petri dishes containing 3 ml of tap water. Approximately 75 larvae were placed in each petri dish. The resulting series of petri dishes was then exposed to light generated by a pair of 40W Cool White Westinghouse fluorescent lamps. Prior to light exposure and at hourly intervals during light exposure, a petri dish was examined for each concentration of erythrosin B. The percent non-swimming larvae was determined as in Example 1 and are tabulated hereinafter in Table IV.

The data of Table IV show a consistent direct relationship between the concentration of erythrosin B and percent non-swimming larvae. It is apparent that a much greater concentration of erythrosin B is necessary to achieve the same effect when the erythrosin B is added directly to the feces. The erythrosin B is much more effective when given by mouth to the animal.

TABLE IV

The effect of erythrosin B on 3rd stage larvae of gastrointestinal nematodes of cattle showing percent non-swimming larvae at varying dosage rates as a function of time of light exposure. In this experiment the dye was added directly to the feces prior to culture and was not given orally to the cattle.

| EXPOSURE IN MINUTES | TREATMENT DOSE | | | | | | | | |
|---|---|---|---|---|---|---|---|---|---|
| | Control | 125 mg/kg | 250 mg/kg | 500 mg/kg | 750 mg/kg | 1000 mg/kg | 1500 mg/kg | 2000 mg/kg | 3000 mg/kg |
| 0 | 9.9 | 7.7 | 11.0 | 7.4 | 6.0 | 9.0 | 4.0 | 4.0 | 7.0 |
| 60 | 17.3 | 33.3 | 20.1 | 28.8 | 25.3 | 40.6 | 51.0 | 78.0 | 98.0 |
| 120 | 19.1 | 40.0 | 26.8 | 49.8 | 46.0 | 64.2 | 98.0 | 100.0 | 100.0 |
| 180 | 21.3 | 44.3 | 45.8 | 54.4 | 70.7 | 84.6 | 100.0 | 100.0 | 100.0 |
| 240 | 22.2 | 42.7 | 57.5 | 65.6 | 91.7 | 90.4 | 100.0 | 100.0 | 100.0 |
| 300 | 20.2 | 52.3 | 67.8 | 67.2 | 94.0 | 91.0 | 100.0 | 100.0 | 100.0 |
| 360 | 20.3 | 62.8 | 71.9 | 85.5 | 96.3 | 96.0 | 100.0 | 100.0 | 100.0 |

Figure 4:
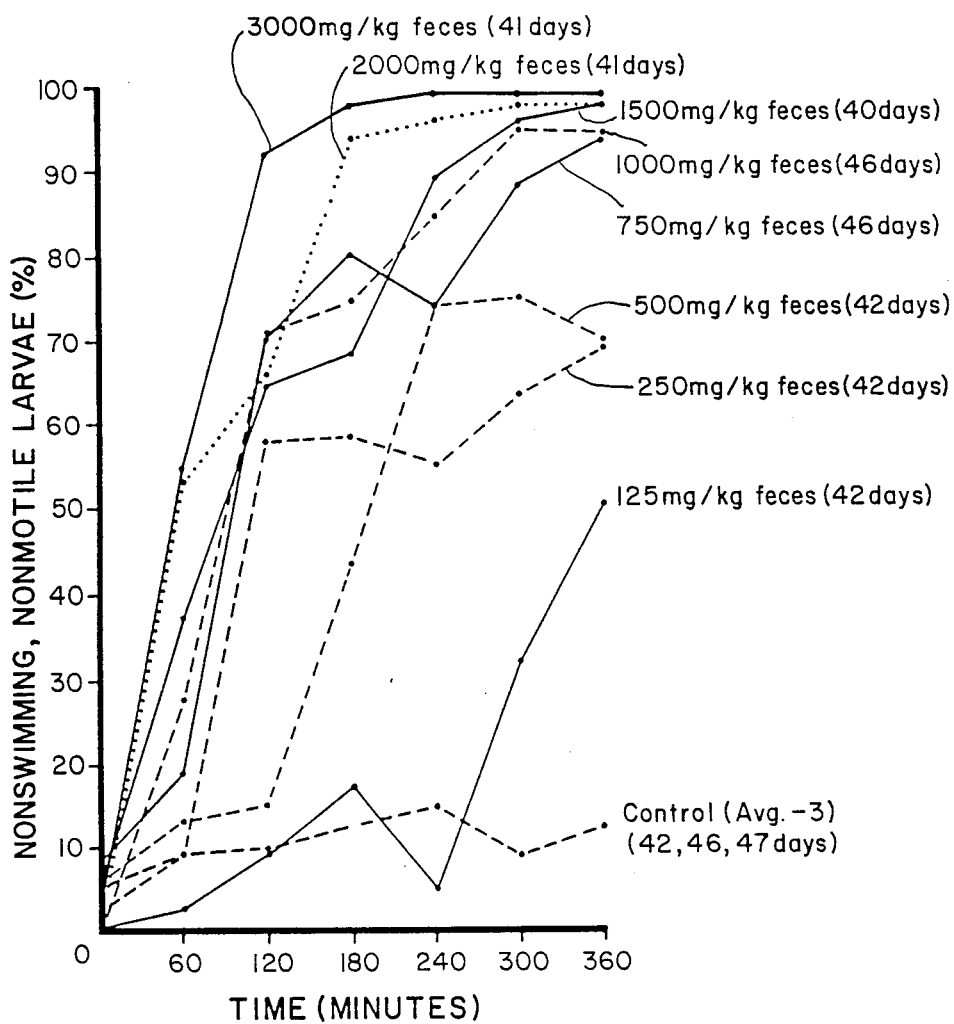

The data of Table IV were used in preparing the graph of FIG. 4 of the drawings. Upon reference to FIG. 4, it may be seen that the graph appearing therein visually illustrates the direct relationship between the concentration of erythrosin B and the percent of non-swimming larvae. Upon comparing FIG. 4 with FIGS. 1-3, it is apparent that a higher concentration of erythrosin B is necessary to achieve the same effect when it is added directly to the feces.

EXAMPLE 3

Feces were collected from a mixed breed calf of approximately 6 months age naturally infected with bovine gastrointestinal nematodes. Vermiculite and tap water were added to the faces to make a mixture suitable for culture. Erythrosin B, phloxin B, eosin yellowish, rose bengal, fluorescein, or rhodamine B dye was added to six portions of the culture at a concentration of 1000 mg/kg of culture. An untreated seventh portion of the culture was maintained as a control. All seven cultures were maintained in the dark until the infective stage had developed (third stage larvae). Infective larvae were then collected from the seven cultures by Baermannization and placed in separate standard petri dishes containing 3 ml of tap water. Approximately 75 larvae were placed in each of the resulting seven petri dishes. The petri dishes were then exposed to light generated by a pair of 40W Cool White Westinghouse fluorescent lamps. Prior to light exposure and at hourly intervals during light exposure, a petri dish was examined for each dye and the level of non-swimming larvae was determined following the general procedure of Example 1. Dishes were evaluated twice, the average value was determined and recorded, and the dish was discarded. The data thus obtained are presented hereinafter in Table V.

These data show that phloxin B and erythrosin B are most effective. Eosin yellowish, rose bengal, and rhodamine B are less effective, while fluorescein is nearly ineffective.

TABLE V

The effect of six xanthene dyes on 3rd stage larvae of gastrointestinal nematodes of cattle showing percent non-swimming larvae as a function of time of light exposure. Dyes were added directly to the feces prior to culture at a rate of 1500 mg/kg of feces.

| EXPOSURE IN MINUTES | TREATMENT | | | | | | |
|---|---|---|---|---|---|---|---|
| | Control | Flourescene | Rose Bengal | Rhodamine | Eosin | Erythrosin | Phloxin |
| 0 | 2.1 | 1.0 | 3.0 | 3.0 | 2.0 | 6.0 | 21.0 |
| 60 | 2.3 | 8.0 | 30.0 | 1.0 | 27.0 | 30.0 | 84.0 |
| 120 | 2.9 | 6.0 | 46.0 | 45.0 | 36.0 | 89.0 | 96.0 |
| 180 | 1.4 | 18.0 | 47.0 | 41.0 | 41.0 | 88.0 | 100.0 |
| 240 | 3.4 | 22.0 | 59.0 | 63.0 | 68.0 | 96.0 | 100.0 |
| 300 | 5.7 | 16.0 | 66.0 | 46.0 | 77.0 | 96.0 | 100.0 |
| 360 | 6.4 | 10.0 | 63.0 | 71.0 | 96.0 | 99.0 | 100.0 |

Figure 5:
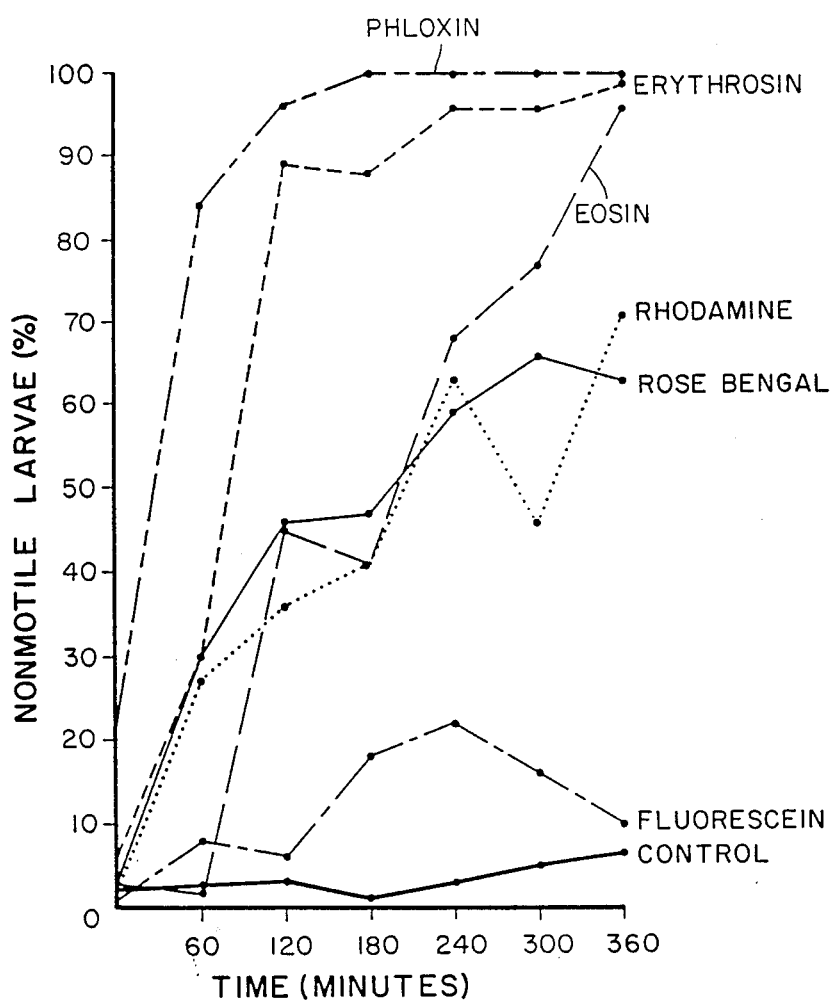

The data of Table V were used in preparing the graph of FIG. 5 of the drawings. Upon reference to FIG. 5, it may be seen that the graph appearing therein visually illustrates the relative effectiveness of the six dyes of this example. The curves for phloxin B and erythrosin B, and to a lesser extent the curve for eosin, show these dyes to be far more effective than the remaining three dyes and the control.

EXAMPLE 4

One mixed breed calf naturally infected with nematodes of mixed species as in Example 1 was treated per os daily with erythrosin B at a dosage level of 40 mg/kg of body weight. Feces were collected daily for each of the first five days while on the erythrosin B treatment. Fecal material collected on each of the five days was incubated separately in the dark for 15 days after which the infective state (third stage larvae) was collected for each day by Baermannization. The larvae were placed in separate petri dishes containing 3 ml of tap water at a density of approximately 75 larvae per dish. Prior to light exposure and at hourly intervals thereafter, the level of non-swimming larvae was evaluated twice for a dish for each day of treatment. The average value was used and the dish was discarded thereafter. The data thus obtained are presented in Table VI.

TABLE VI

The effect of erythrocin B on 3rd stage larvae of gastrointestinal nematodes of cattle showing percent non-swimming larvae as a function of time of light exposure comparing the effect of the number of consecutive days of treatment.

| EXPOSURE IN MINUTES | TREATMENT | | | | | |
|---|---|---|---|---|---|---|
| | Control | 1 day | 2 days | 3 days | 4 days | 5 days |
| 0 | 6.7 | 3.0 | 4.0 | 2.0 | 7.5 | 10.0 |
| 60 | 8.3 | 3.0 | 26.0 | 9.0 | 14.0 | 16.0 |
| 120 | 12.7 | 6.5 | 30.0 | 28.0 | 40.5 | 30.0 |
| 180 | 10.0 | 8.0 | 36.0 | 39.4 | 69.5 | 52.0 |
| 240 | 17.3 | 6.0 | 46.0 | 50.0 | 83.0 | 97.0 |
| 300 | 19.3 | 12.5 | 73.0 | 86.0 | 95.0 | 98.0 |
| 360 | 22.0 | 22.0 | 89.0 | 95.0 | 99.0 | 100.0 |

The data of Table VI show that higher levels of the erythrosin B is passed into the feces beginning on the second day after initiation of treatment thereby resulting in excellant control of the third stage nematodes.

Figure 6:
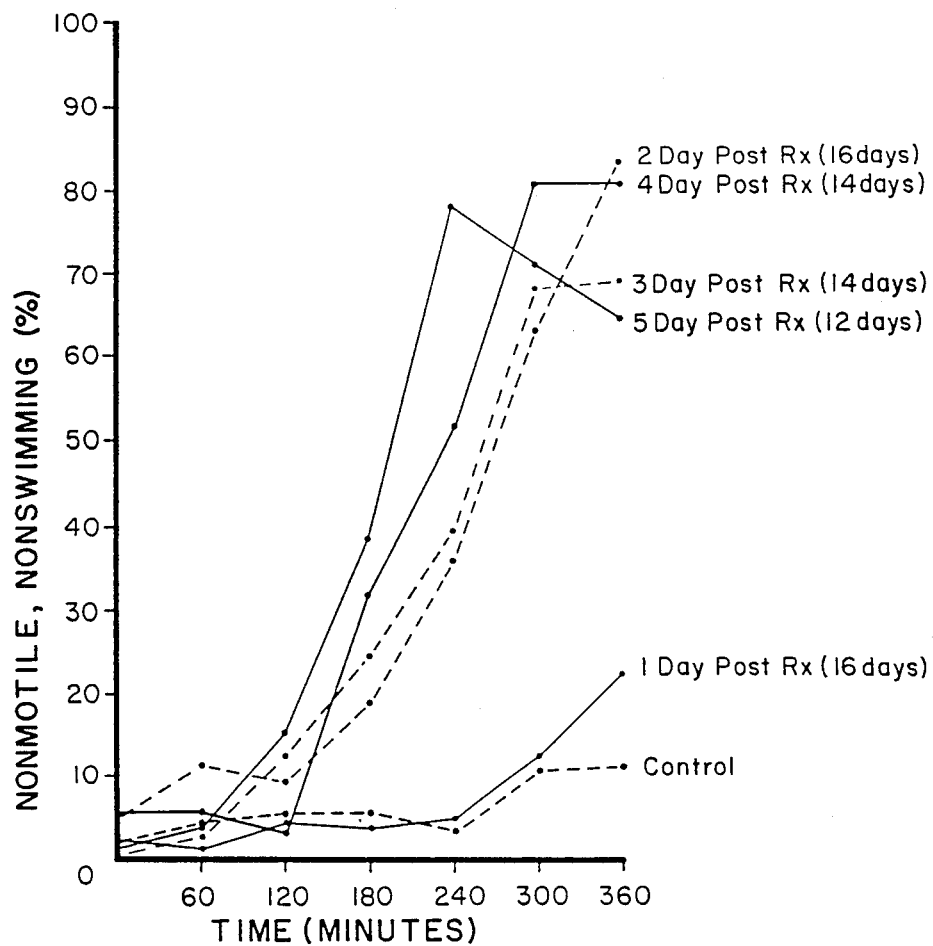

The data of Table VI were used in preparing the graph of FIG. 6 of the drawings. Upon reference to FIG. 6, it may be seen that the results obtained for the second through the fifth days of treatment are far superior to the control and the first day of treatment.

EXAMPLE 5

Erythrosin B was given per os at a rate of 30 mg/kg of body weight to a mixed breed calf of approximately six months of age which was naturally infected with bovine gastrointestinal nematodes as in Example 1. Fecal material was collected post treatment and was set up for culture as previously described in Example 1. After approximately 15 days of incubation, third stage larvae was collected by Baermannization and placed in petri dishes containing approximately 75 larvae in 3 ml of tap water. A first series of petri dishes was prepared containing erythrosin B treated larvae, and a second series of petri dishes was prepared containing untreated larvae from the control. The first and second series of petri dishes were placed uncovered in direct sunlight at 11:15 a.m. The percent of non-swimming larvae was visually scored after 15, 30 and 45 minutes of sunlight exposure using a dissection microscope.

The percent non-swimming (dead) larvae reached 90% after 30 minutes of sunlight exposure and approached 100% after 45 minutes of sunlight exposure for the erythrosin B treated larvae, whereas the result of the control were markedly lower. These data show that direct sunlight initiates a lethal reaction to erythrosin B treated infective larvae of gastrointestinal nematodes of cattle. Direct sunlight appears to be much more effective in the initiation of this reaction than the controlled light source utilized in the laboratory studies of Examples 1-4.

We claim:

1. A method of combatting internal parasites of warm blooded animals, said parasites being selected from the group consisting of endoparasitic helminths and pathogenic gastrointestinal protozoa having a life cycle which includes a life stage within said animals and a life stage outside of said animals, said parasites normally being protected from exposure to natural electromagnetic radiation having a wave length falling within the visible spectrum during at least most of said life stage within the animals and normally being exposed to said electromagnetic radiation during at least a portion of said life stage outside of the animals, comprising orally administering to a said warm blooded animal infected with a said internal parasite at least one dye promoting the formation of cytotoxic oxygen upon exposure to electromagnetic radiation having a wave length falling within the visible spectrum absorbed thereby in the presence of molecular oxygen, the said parasite being capable of incorporating therein said dye and said dye being administered to said animal in an amount effective to cause said parasite to incorporate therein a photosensitizing amount of said dye during said life stage within said animal, and thereafter during said life stage outside of said animal said parasite having said photosensitizing amount of dye incorporated therein being exposed to said electromagnetic radiation having a wave length falling within the visible spectrum absorbed by said dye in the present of molecular oxygen to thereby form cytotoxic oxygen and initiate at least one lethal oxidative reaction within the resulting photosensitized parasite and break the life cycle of said parasite.

2. The method of claim 1 wherein said animals are selected from the group consisting of Ruminantia, Equidae, Suidae, Galliforms, Canidae and Felidae.

3. The method of claim 1 wherein said parasites are selected from the group consisting of nematodes, platyhelminths, amoebidae and coccidia.

4. The method of claim 1 wherein the said parasites are selected from the group consisting of Metastrongylidea, Ascaroidea, Trichostrongyloidea, Strongyloidea, Trichuroidea, Oxyuroidea, and Rhabditoidea.

5. The method of claim 1 wherein the said animals are cattle and said parasites are selected from the group consisting of *Ostertagia ostertagi, Trichostrongylus sp., Cooperia sp., Oesophagostomum radiatum, Bunostomum phlebotomum, Haemonchus sp.* and *Trichuris sp.*

6. The method of claim 1 wherein the said dye is a xanthene dye.

7. The method of claim 1 wherein the said dye is a xanthene dye selected from the group consisting of phloxin B, erythrosin B, eosin yellowish, rose bengal and rhodamine B.

8. The method of claim 1 wherein the said animals are poultry and the said parasites are coccidia.

9. The method of claim 7 wherein the said animals are cattle and the said parasites are selected from the group consisting of *Ostertagia ostertagi, Trichostrongylus sp., Cooperia sp., Oesophagostomum radiatum, Bunostomum phlebotomum, Haemonchus sp.* and *Trichuris sp.*

10. The method of claim 8 wherein the said dye is a xanthene dye selected from the group consisting of phloxin B, erythrosin B, eosin yellowish, rose bengal and rhodamine B.

11. The method of claim 1 wherein about 0.01-100 milligrams of said dye per kilogram of body weight is administered to said animal.

12. The method of claim 1 wherein about 0.01-100 milligrams of said dye per kilogram of body weight is administered to said animal.

13. The method of claim 1 wherein about 0.01-100 milligrams of said dye per kilogram of body weight is administered to said animal.

14. The method of claim 1 wherein at least one sensitizing dye for photographic film which promotes the formation of cytotoxic oxygen is also administered to the said animal.

15. The method of claim 1 wherein at least one desensitizing dye for photographic film which promotes the formation of cytotoxic oxygen is also administered to the said animal.

16. The method of claim 1 wherein at least one sensitizing dye for photographic film which promotes the formation of cytotoxic oxygen and at least one desensitizing dye for photographic film which promotes the formation of cytotoxic oxygen are also administered to the said animal.

17. The method of claim 1 wherein a plurality of said dyes are administered to the said animal, and said plurality of dyes each have different absorption spectra whereby the formation of cytotoxic oxygen is promoted.

18. The method of claim 17 wherein at least one sensitizing dye for photographic film which promotes the formation of cytotoxic oxygen is also administered to the said animal.

19. The method of claim 17 wherein at least one desensitizing dye for photographic film which promotes the formation of cytotoxic oxygen is also administered to the said animals.

20. The method of claim 17 wherein at least one sensitizing dye for photographic film which promotes the formation of cytotoxic oxygen and at least one desensitizing dye for photographic film which promotes the formation of cytotoxic oxygen are also administered to the said animal.

* * * * *